United States Patent [19]

Friden

[11] Patent Number: 5,154,924
[45] Date of Patent: Oct. 13, 1992

[54] TRANSFERRIN RECEPTOR SPECIFIC ANTIBODY-NEUROPHARMACEUTICAL AGENT CONJUGATES

[75] Inventor: Phillip Friden, Bedford, Mass.

[73] Assignee: Alkermes, Inc., Cambridge, Mass.

[21] Appl. No.: 404,089

[22] Filed: Sep. 7, 1989

[51] Int. Cl.$^5$ .................. A61K 39/44; A61K 37/48; C07K 17/02; C12N 11/06
[52] U.S. Cl. .................. 424/85.91; 424/85.2; 424/85.8; 424/94.3; 435/188; 530/302; 530/311; 530/370; 530/351; 530/388.22; 530/391.1; 530/391.3; 530/391.5; 530/391.7; 530/391.9; 530/399
[58] Field of Search .................. 424/85.2, 85.8, 85.91, 424/94.3; 435/188; 530/302, 311, 370, 351, 390, 391, 399, 391.7, 391.9, 391.1, 391.3, 391.5, 388.22

[56] References Cited

U.S. PATENT DOCUMENTS

| | | | |
|---|---|---|---|
| 4,434,156 | 2/1984 | Trowbridge | 424/85.91 |
| 4,545,985 | 10/1985 | Pastan et al. | 424/85.91 |
| 4,569,789 | 2/1986 | Blattler et al. | 424/85.91 |
| 4,626,507 | 12/1986 | Trowbridge | 435/240 |
| 4,631,190 | 12/1986 | Shen et al. | 424/85.91 |

FOREIGN PATENT DOCUMENTS

| | | |
|---|---|---|
| 253202 | 1/1988 | European Pat. Off. |
| 286441 | 10/1988 | European Pat. Off. |
| 1564666 | 4/1980 | United Kingdom |

OTHER PUBLICATIONS

Trowbridge et al; *Nature* vol. 294, No. 12, pp. 171–173 (Nov. 1981).
Domingo et al; *Methods in Enzymology*, vol. 112, pp. 238–247 (1985).
Zovickian et al; *J. Neurosurg* 66: 850–861 (1987).
Jefferies, W. A., et al., *Nature*, 312(8): 162–163 (1984).
Raso, V., et al., *Biochem. Biophy. Res. Comm.*, 150(1): 104–110 (1988).
Bjorn et al (1987) Cancer Res 47:6639–6645.
Griffin et al (1988) J. Biol. Res. Mod. 7:559–567.
Alkan et al (1984) J. Tuterferon Res 4(3):355–363.
Capon et al. (1989) Nature 337:525–531.
Pietersz et al (1988) Cancer Res 48:4469–76.
Pietersz et al (1987) Immunol Cell Biol 65 (pt 2):111–125.
Gascoigne et al (1987) Proc Natl Acad Sci USA 84:2936–2940.
Baldwin et al (1983) Bull. Cancer (Paris) 70(2):132–136.
Byrn et al (1990) Nature 344:667–670.
Dantry-Varsat et al (1983) PNAS USA 80:2258–2262.

*Primary Examiner*—Christine M. Nucker
*Assistant Examiner*—Kay K. Kim
*Attorney, Agent, or Firm*—Hamilton, Brook, Smith & Reynolds

[57] ABSTRACT

The present invention pertains to a method for delivering a neuropharmaceutical agent across the blood brain barrier to the brain of a host. The method comprises administering to the host a therapeutically effective amount of an antibody-neuropharmaceutical agent conjugate wherein the antibody is reactive with a transferrin receptor. Other aspects of this invention include a delivery system comprising an antibody reactive with a transferrin receptor linked to a neuropharmaceutical agent and method for treating hosts afflicted with a disease associated with a neurological disorder.

13 Claims, No Drawings

TRANSFERRIN RECEPTOR SPECIFIC ANTIBODY-NEUROPHARMACEUTICAL AGENT CONJUGATES

BACKGROUND

The capillaries that supply blood to the tissues of the brain constitute the blood brain barrier (Goldstein et al. (1986) Scientific American 255:74-83; Pardridge, W.M. (1986) Endocrin Rev. 7:314-330). The endothelial cells which form the brain capillaries are different from those found in other tissues in the body. Brain capillary endothelial cells are joined together by tight intercellular junctions which form a continuous wall against the passive movement of substances from the blood to the brain. These cells are also different in that they have few pinocytic vesicles which in other tissues allow somewhat unselective transport across the capillary wall. Also lacking are continuous gaps or channels running through the cells which would allow unrestricted passage.

The blood-brain barrier functions to ensure that the environment of the brain is constantly controlled. The levels of various substances in the blood, such as hormones, amino acids and ions, undergo frequent small fluctuations which can be brought about by activities such as eating and exercise (Goldstein et al, cited supra). If the brain were not protected by the blood brain barrier from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated receptors which, upon binding of their respective ligand, are internalized by the cell (Pardridge, W.M., cited supra). Vesicles containing the receptor-ligand complex then migrate to the abluminal surface of the endothelial cell where the ligand is released.

The problem posed by the blood-brain barrier is that, in the process of protecting the brain, ituexcludes many potentially useful therapeutic agents. Presently, only substances which are sufficiently lipophilic can penetrate the blood-brain barrier (Goldstein et al, cited supra; Pardridge, W.M., cited Supra). Some drugs can be modified to make them more lipophilic and thereby increase their ability to cross the blood brain barrier. However, each modification has to be tested individually on each drug and the modification can alter the activity of the drug. The modification can also have a very general effect in that it will increase the ability of the compound to cross all cellular membranes, not only those of brain capillary endothelial cells.

SUMMARY OF THE INVENTION

The present invention pertains to a method for delivering a neuropharmaceutical agent across the blood brain barrier to the brain of a host. The method comprises administering to the host a therapeutically effective amount of an antibody-neuropharmaceutical agent conjugate wherein the antibody is reactive with a transferrin receptor. The conjugate is administered under conditions whereby binding of the antibody to a transferrin receptor on a brain capillary endothelial cell occurs and the neuropharmaceutical agent is transferred across the blood brain barrier in a pharmaceutically active form. Other aspects of this invention include a delivery system comprising an antibody reactive with a transferrin receptor linked to a neuropharmaceutical agent and methods for treating hosts afflicted with a disease associated with a neurological disorder.

Presently available means for delivering therapeutic agents to the brain are limited in that they are invasive. The delivery system of the present invention is non-invasive and can utilize readily available antibodies reactive with a transferrin. receptor as carriers for neuropharmaceutical agents. The delivery system is advantageous in that the antibodies are capable of transporting neuropharmadeutical agents across the blood brain barrier without being susceptible to premature release of the neuropharmaceutical agent prior to reaching the brain-side of the blood brain barrier. Further, if the therapeutic activity of the agent to be delivered to the brain is not altered by the addition of a linker, a noncleavable linker can be used to link the neuropharmaceutical agent to the antibody.

DETAILED DESCRIPTION

The method for delivering a neuropharmaceutical agent across the blood brain barrier to the brain of a host comprises administering to the host a therapeutically effective amount of an antibody-neuropharmaceutical agent conjugate wherein the antibody is reactive with a transferrin receptor present on a brain capillary endothelial cell. The method is conducted under conditions whereby the antibody binds to the transferrin receptor on the brain capillary endothelial cell and the neuropharmaceutical agent is transferred across the blood brain barrier in a pharmaceutically active form.

The host can be an animal susceptible to a neurological disorder (i.e., an animal having a brain). Examples of hosts include mammals such as humans, domestic animals (e.g., dog, cat, cow or horse), mice and rats.

The neuropharmaceutical agent can be an agent having a therapeutic or prophylatic effect on a neurological disorder. Examples of neurological disorders include cancer (e.g. brain tumors), Autoimmune Deficiency Syndrome (AIDS). epilepsy. Parkinson's disease, multiple sclerosis, neurodegenerative disease, trauma, depression, Alzheimer's disease, migraine, pain, or a seizure disorder. Classes of neuropharmaceutical agents which can be used in this invention include proteins, antibiotics, adrenergic agents, anticonvulsants, small molecules, nucleotide analogs. chemotherapeutic agents, anti-trauma agents, peptides and other classes of agents used to treat or prevent a neurological disorder. Examples of proteins include CD4, growth factors (e.g. nerve growth factor and interferon), dopamine decarboxylase and tricosanthin. Examples of antibiotics include amphotericin B, gentamycin sulfate, and pyrimethamine. Examples of adrenergic agents (including blockers) include dopamine and atenolol. Examples of chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of peptides would be somatostatin analogues and enkephalinan inhibitors.

Nucleotide analogs which can be used include azido thymidine (hereinafter AZT), dideoxy Inosine (ddI) and dideoxy cytodine (ddc).

Serum transferrin is a monomeric glycoprotein with a molecular weight of 80,000 daltons that binds iron in the circulation and transports it to the various tissues(Aisen et al. (1980) *Ann. Rev. Biochem.* 49 357.393; MacGillivray et al. (1981) *J. Biol. Chem.* 3543.3553). The uptake of iron by individual cells is mediated by the transferrin receptor, an integral membrane glycoprotein consisting of two identical 95,000 dalton subunits that are linked by a disulfide bond. The number of receptors on the surface of a cell appears to correlate with cellular proliferation, with the highest number being on actively growing cells and the lowest being on resting and terminally differentiated cells. Jeffries et al (*Nature* Vol. 312 (November 1984) pp. 167–168) used monoclonal antibodies to show that brain capillary endothelial cells have transferrin receptors on their cell surface.

Antibodies which can be used within this invention are reactive with a transferrin receptor. The term antibody is intended to encompass both polyclonal and monoclonal antibodies. The preferred antibody is a monoclonal antibody reactive with a transferrin receptor. The term antibody is also intended to encompass mixtures of more than one antibody reactive with a transferrin receptor (e.g.. a cocktail of different types of monoclonal antibodies reactive with a transferrin receptor. The term antibody is further intended to encompass whole antibodies, biologically functional fragments thereof, and chimeric antibodies comprising portions from more than one species. Biologically functional antibody fragments which can be used are those fragments sufficient for binding of the antibody fragment to the transferrin receptor to occur.

The chimeric antibodies can comprise portions derived from two different species (e.g., human constant region and murine binding region). The portions derived from two different species can be joined together chemically by conventional techniques or can be prepared as a single contiguous protein using genetic engineering techniques. DNA encoding the proteins of both portions of the chimeric antibody can be expressed as a contiguous protein.

The term transferrin receptor is intended to encompass the entire receptor or portions thereof. Portions of the transferrin receptor include those portions sufficient for binding of the receptor to an anti-transferrin receptor antibody to occur.

Monoclonal antibodies reactive with at least a portion of the transferrin receptor can be obtained (e.g., OX.26, B3/25 (Omary et al. (1980) *Nature* 286,888–891), T56/14 (Gatter et al. (1983) *J. Clin. Path.* 36 539–545; Jefferies et al. *Immunology* (1985) 54:333–341), OKT.9 (Sutherland et al. (1981) *Proc. Natl. Acad. Sci. USA* 78:4515.4519), L5.1 (Rovera, C. (1982) *Blood* 59:671.678), 5E.9 (Haynes et al. (1981) *J. Immunol.* 127:347 351), RI7 217 (Trowbridge et al. *Proc. Natl. Acad. Sci. USA* 78:3039 (1981) and T58/30 (Omary et al. cited supra) or can produced using conventional somatic cell hybridization techniques (Kohler and Milstein (1975) *Nature* 256, 495.497). A crude or purified protein or peptide comprising at least a portion of the transferrin receptor can be used as the immunogen. An animal is vaccinated with the immunogen to obtain an anti-transferrin receptor antibody-producing spleen cells. The species of animal immunized will vary depending on the species of monoclonal antibody desired.

The antibody producing cell is fused with an immortalizing cell (e.g. myeloma cell) to create a hybridoma capable of secreting anti transferrin receptor antibodies. The unfused residual antibody-producing cells and immortalizing cells are eliminated. Hybridomas producing the anti-transferrin receptor antibodies are selected using conventional techniques and the selected anti tranferrin receptor antibody producing hybridomas are cloned and cultured.

Polyclonal antibodies can be prepared by immunizing an animal with a crude or purified protein or peptide comprising at least a portion of a transferrin receptor. The animal is maintained under conditions whereby antibodies reactive with a transferrin receptor are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g. IgG, IgM).

The neuropharmaceutical agent can be linked to the antibody using standard chemical conjugation techniques. Generally, the link is made via an amine or a sulfhydryl group. The link can be a cleavable link or non-cleavable link depending upon whether the neuropharmaceutical agent is more effective when released in its native form or whether the pharmaceutical activity of the agent can be maintained while linked to the antibody. The determination of whether to use a cleavable or non-cleavable linker can be made without undue experimentation by measuring the activity of the drug in both native and linked forms or for some drugs can be determined based on known activities of the drug in both the native and linked form.

For some cases involving the delivery of proteins or peptides to the brain, release of the free protein or peptide may not be necessary if the biologically active portion of the protein or peptide is uneffected by the link. As a result, antibody-protein or antibody peptide conjugates can be constructed using noncleavable linkers. Examples of such proteins or peptides include CD4, superoxide dismutase, interferon, nerve growth factor, tricosanthin, dopamine decarboxylase, somatostatin analogues and enkephalinase inhibitors. Examples of non-cleavable linker systems which can be used in this invention include the carbodiimide (EDC), the sulfhydryl-maleimide, the N.succinimidyl.3.(2-pyridyldithio) propionate (SPDP; Pharmacia), and the periodate systems. In the carbodiimide system, a water soluble carbodiimide reacts with carboxylic acid groups on proteins and activates the carboxyl group. The carboxyl group is coupled to an amino group of the second protein. The result of this reaction is a noncleavable amide bond between two proteins.

In the sulfhydryl.maleimide system, a sulfhydryl group is introduced onto an amine group of one of the proteins using a compound such as Traut's reagent. The other protein is reacted with an NHS ester (such as gamma-maleimidobutyric acid NHS ester (GMBS)) to form a maleimide derivative that is reactive with sulfhydryl groups. The two modified proteins are then reacted to form a covalent linkage that is noncleavable.

SPDP is a heterofunctional crosslinking reagent that introduces aliphatic thiol groups into either the monoclonal antibody or the neuropharmaceutical agent. The thiol group reacts with an amine group forming a noncleavable bond.

Periodate coupling requires the presence of oligosaccharide groups on either the carrier or the protein to be delivered. If these groups are available on the protein to be delivered (as in the case of horseradish peroxidase (HRP)), an active aldehyde is formed on the protein to be delivered which can react with an amino group on the carrier. It is also possible to form active aldehyde groups from the carbohydrate groups present on antibody molecules. These groups can then be reacted with amino groups on the protein to be delivered generating a stable conjugate. Alternatively, the periodate oxidized antibody can be reacted with a hydrazide derivative of a protein to be delivered which will also yield a stable conjugate.

The antibody-protein conjugate can also be produced as a contiguous protein using genetic engineering techniques. Gene constructs can be prepared comprising DNA encoding the anti-transferrin receptor antibody fused to DNA encoding the protein to be delivered across the blood brain barrier. The protein can be expressed as a contiguous molecule containing both an antibody portion and a neuropharmaceutical agent portion.

Cleavable linkers can be used to link neuropharmaceutical agents which are to be deposited in the brain or when a non-cleavable linker alters the activity of a neuropharmaceutical agent. Examples of cleavable linkers include the acid labile linkers described in copending patent application Ser. No. 07/308,960 filed February 6, 1989, the contents of which are hereby incorporated by reference. Acid labile linkers include cis aconitic acid, cis-carboxylic alkadienes, cis-carboxylic alkatrienes, and poly-maleic anhydrides. Other cleavable linkers are linkers capable of attaching to primary alcohol groups. Examples of neuropharmaceutical agents which can be linked via a cleavable link include AZT, ddI, ddc, adriamycin, amphotericin B, pyrimethamine, valproate, methotrexate, cyclophosphamide, carboplatin and superoxide dimutase. The noncleavable linkers used generally to link proteins to the antibody can also be used to link other neuropharmaceutical agents to the antibody.

The antibody-neuropharmaceutical agent conjugates can be administered orally, by subcutaneous or other injection, intravenously, intramuscularly, parenternally, transdermally, nasally or rectally. The form in which the conjugate is administered (e.g., capsule, tablet, solution, emulsion) will depend at least in part on the route by which it is administered.

A therapeutically effective amount of an antibody-neuropharmaceutical agent conjugate is that amount necessary to significantly reduce or eliminate symptoms associated with a particular neurological disorder. The therapeutically effective amount will be determined on an individual basis and will be based. at least in part, on consideration of the individuals's size, the severity of symptoms to be treated, the result sought, the specific antibody, etc. Thus, the therapeutically effective amount can be determined by one of ordinary skill in the art employing such factors and using no more than routine experimentation The present invention will be illustrated by the following examples.

EXAMPLE 1

In Vitro Binding of Murine Monoclonal Antibodies to Human Brain Endothelial Cells Two murine monoclonal antibodies, B3/25 and T58/30, described by Trowbridge (U.S. Pat. No. 4,434,156 issued February 28, 1984, and *Nature* Vol. 294, pp. 171-173 (1981)), the contents of both are hereby incorporated by reference, which recognize the human transferrin receptor were tested for their ability to bind to human brain capillary endothelial cells. Hybridoma cell lines which produce B3/25 and T58/30 antibodies were obtained from the American Type Culture Collection (ATTC) in Rockville, Maryland, and grown in DMEM medium supplemented with 2.0 mM glutamine, 10.0 mM HEPES (pH 7.2), 100 $\mu$M nonessential amino acids and 10% heat-inactivated fetal calf serum. The hybridoma cultures were scaled-up in 225 $cm^2$ T.flasks for the production of milligram quantities of IgG antibody. The hybridoma supernatants were concentrated 50x using vacuum dialysis and applied to a protein-A sepharose column using the BioRad MAPS buffer system. Purified antibody was eluted from the column, dialyzed against 0.1 M sodium phosphate (pH 8.0), concentrated and stored in aliquots at −20° C.

Primary cultures of human brain endothelial cells were grown in flat-bottom 96-well plates until five days post-confluency. The cells were then fixed using 3.0% buffered formalin and the plate blocked with 1.0% bovine serum albumin (BSA) in Dulbecco's phosphate buffered saline (DPBS). Aliquots (100 $\mu$l) of the B3/25 or T58/30 antibodies, either in the form of culture supernatants or purified protein, were then added to the wells (antibody concentrations were in the range of 1-50 $\mu$g/ml). Antibody which had specifically bound to the fixed cells was detected using a biotin-labeled polyclonal goat-anti-mouse IgG antisera followed by a biotinylated horseradish peroxidase (HRP)/avidin mixture (Avidin Biotin Complex technique). Positive wells were determined using a Titertek Multiscan Enzyme Linked Immunosorbent Assay (ELISA) plate reader. The results showed that both antibodies bind to human brain capillary endothelial cells with the T58/30 antibody exhibiting a higher level of binding.

These same antibodies were also tested for binding to human brain capillaries using sections of human brain tissue that were fresh frozen (without fixation), sectioned on a cryostat (section thickness was 5-20 $\mu$m), placed on glass slides and fixed in acetone (10 minutes at room temperature). These sections were then stored at −20° C. prior to use.

The slides containing the human brain sections were allowed to come to room temperature prior to use. The sections were then rehydrated in DPBS and incubated in methanol containing 0.3% $H_2O_2$ to block endogenous peroxidate activity. The sections were blocked for fifteen minutes in a solution containing 0.2% non-fat dry milk and 0.2% methylmannopyranoside. B3/25 and T58/30 antibodies, purified as discussed above, were applied to the sections at a concentration of 5-50 $\mu$g/ml and incubated at room temperature for one to two hours. Antibody that specifically bound to the tissue was detected using the Avidin-Biotin Complex (ABC) technique as described above for the ELISA assay. Staining of capillaries in the human brain sections was observed with both the B3/25 and T58/30 antibodies.

The T58/30 antibody also displayed some binding to the white matter of the brain cortex.

EXAMPLE 2

In-Vitro Binding of Murine Monoclonal Antibody OX-26 to Rat Transferrin Receptor The OX-26 murine antibody, which recognizes the rat transferrin receptor, has been shown in vivo to bind to brain capillary endothelial cells (Jeffries et al., cited supra). The murine hybridoma line which produces the OX.26 murine antibody was obtained and the hybridoma cell line was grown in RPMI 1640 medium supplemented with 2.0 mM glutamine and 10% heat-inactivated fetal calf serum. The OX.26 antibody was purified using the affinity chromatography technique described in Example 1.

The purified antibody was tested in vitro as described for the anti-human transferrin receptor antibodies in Example 1 to determine whether it would bind to brain capillaries in fresh frozen, acetone-fixed rat brain sections. The results showed that the OX.26 anti transferrin receptor antibody did bind to capillaries in rat brain sections in vitro.

EXAMPLE 3

In-Vivo Binding of OX 26 Murine Monoclonal Antibody to Rat Transferrin Receptor

Dose Range

The rat anti transferrin receptor antibody OX-26 was tested in vivo by injecting purified antibody (purification as described in Example 1) into female Sprague-Dawley rats (100–150 gm) via the tail vein. Prior to injection, the rats were anesthetized with halothane. The samples, ranging from 2.0 mg to 0.05 mg of antibody/rat were injected into the tail vein in 400 μl aliquots. All doses were tested in duplicate animals. One hour postinjection, the animals were sacrificed and perfused through the heart with DPBS to clear the blood from the organs. Immediately after the perfusion was completed, the brain was removed and quick frozen in liquid nitrogen. The frozen brain was then sectioned (30–50 μm) on a cryostat and the sections placed on glass microscope slides. The brain sections were air dried at room temperature one to two hours before fixation in acetone (10 minutes at room temperature). After this treatment the sections could be stored at −20° C.

The OX-26 antibody was localized in the brain sections using immunohistochemistry as described above for the in vivo experiments in Example 1. The addition of the primary antibody was unnecessary in that it is present in the brain sections. The results indicated that the OX.26 antibody binds to rat brain capillary endothelial cells and that as little as 50 μg can be detected in the brain using the methods described herein. Doses above 0.5 mg did not appear to show significantly more antibody binding to the endothelial cells, suggesting that the sites for antibody binding may be saturated. No specific binding to capillary endothelium was detected in the liver, kidney, heart, spleen or lung.

A non-specific antibody of the same subclass as OX-26 (IgG 2a) was also tested in vivo to show that the binding of OX.26 to rat brain endothelial cells that has been observed is specific to the OX-26 antibody. 0.5 mg of the control antibody was injected per rat as described above. The results indicate that the staining pattern observed with the OX-26 antibody is specific to that antibody.

Time Course

After establishing that the OX.26 antibody is detectable in the rat brain capillaries after in vivo administration, the time frame in which this binding occurred was determined. Using 0.5 mg of purified OX-26 antibody as the standard dose, brain sections taken from animals sacrificed 5 minutes, 15 minutes, 1 hour, 2 hours, 4 hours, 8 hours and 24 hours post injection were examined for the presence of OX.26 antibody. All doses were administered in 400 μl aliquots and each time point was tested in duplicate animals. Samples were injected and the rats were processed at the various times post-injection as described above in the dose range section.

The results showed that the OX.26 antibody can be detected in or on the rat brain capillary endothelial cells as early as five minutes and as late as 24 hours post-injection. At 4 and 8 hours post-injection, the staining pattern of the antibody is very punctate suggesting that the antibody has accumulated in pericytes.

EXAMPLE 4

The Use of OX.26 Murine Monoclonal Antibody As A Carrier for Transferring Horseradish Peroxidase Across the Blood Brain Barrier Horseradish Peroxidase (HRP; 40 kD) was chosen as a compound to be delivered to the brain because it is similar in size to several therapeutic agents, (e.g. CD4), and it can be easily detected in the brain using an enzymatic assay. HRP was conjugated to the OX-26 antibody using a non-cleavable periodate linkage and the ability of the antibody to function as a carrier of compounds to the brain was examined. The antibody conjugate was tested in vivo to determine if the antibody could deliver HRP to the brain The OX-26 antibody was coupled to HRP using a periodate linkage. The antibody (10 mg) was first dialyzed overnight against 0.01 M sodium bicarbonate (pH 9.0). The HRP (10 mg) was dissolved in 2.5 ml deionized water, 0.1 M sodium periodate (160 μl) was added and the mixture was incubated for five minutes at room temperature. Ethylene glycol (250 μl) was added to the HRP solution followed by an additional five minute incubation. This solution was then dialyzed overnight against 1.0 mM sodium acetate buffer (pH 4.4). To the dialyzed OX-26 antibody (2.0 ml, 5.08 mg/ml) was added 200 μl of 1.0 M sodium bicarbonate buffer, pH 9.5 and 1.25 ml of the dialyzed HRP solution. This mixture was incubated in the dark for two hours followed by the addition of 100 μl of 10 mg/ml sodium borohydride. The resulting mixture was incubated two additional hours in the dark at 4° C. The protein was precipitated from the solution by the addition of an equal volume of saturated ammonium sulfate and resuspended in a minimal volume of water. Free antibody was removed from the mixture by chromatography on a concanavalin A-sepharose column (a column which binds HRP and the HRP-antibody conjugate and allows the free antibody to pass through). The free HRP was removed by chromatography on a protein A-sepharose column which retains the antibody-HRP conjugate. The final product had an HRP/antibody ratio of 4/1.

A time course experiment identical to that described in Example 3 was performed using the antibody-HRP conjugate. The antibody-HRP conjugate (0.5 mg) was injected in a 400 μl aliquot/rat. The (0.5 mg) animals were sacrificed at the various times post-injection and the brains processed as described above in Example 3. The antibody HRP conjugate was localized in the brain either by staining for antibody immunohistochemically as described in Example 1 or by directly staining the brain sections for the presence of HRP. To detect HRP, the slides were first allowed to come to room temperature before incubating in methanol for thirty minutes. The brain sections were then washed in DPBS and reacted with 3,3'-diamino benzidine (DAB), the substrate for HRP. The results showed that the OX-26 antibody HRP conjugate binds to rat brain capillary endothelial cells in a manner identical to that of the unconjugated antibody. The punctate staining 4-8 hours after injection which was seen with the antibody alone is also seen with the antibody conjugate, suggesting that the conjugate can also be going into the pericytes on the abluminal side of the blood brain barrier. Taken together, these results indicate that the OX-26 antibody can deliver a protein molecule of at least 40 KD to the brain.

EXAMPLE 5

The In-Vivo Delivery of Adriamycin to the Brain by Murine Monoclonal Antibody OX-26

A non-cleavable linker system similar to that used in Example 4, was used to couple the chemotherapeutic drug adriamycin to the OX-26 antibody. The availability of antibodies that can detect adriamycin as well as the system previously described in Example 1 for detecting the antibody carrier allowed the use of immunohistochemical techniques for monitoring the localization of the antibody carrier as well as the delivery of adriamycin to the brain.

To conjugate adriamycin to the antibody, the drug (10 mg in 0.5 ml DPBS) was oxidized by the addition of 200$\mu$l of 0.1 M sodium periodate. This mixture was incubated for one hour at room temperature in the dark. The reaction was quenched by the addition of 200 $\mu$l of ethylene glycol followed by a five minute incubation. The OX-26 antibody (5.0 mg in 0.5 ml of carbonate buffer (pH 9.5)) was added to the oxidized adriamycin and incubated at room temperature for one hour. Sodium borohydride (100 $\mu$l of 10 mg/ml) was added and the mixture was incubated for an additional two hours at room temperature. The free adriamycin was separated from the OX-26 antibody-adriamycin conjugate by chromatography on a PD.10 column. The adriamycin/OX.26 antibody ratio within the conjugate was 2/1. for this particular batch of conjugate.

The effectiveness of the OX.26 antibody as a carrier for delivering adriamycin to the brain was determined by administering 0.5 mg of the antibody-adriamycin conjugate in a 400 $\mu$l aliquot per rat by injection via the tail vein. One hour post-injection, the rat was sacrificed and the brain processed as described in Example 1. All injections were performed in duplicate. As a control, 400 $\mu$g of free adriamycin in a 400 $\mu$l aliquot was also injected into a rat. Immunohistochemistry was used to detect both the carrier OX.26 antibody and the adriamycin in the rat brain sections. In the case of adriamycin, polyclonal rabbit anti-adriamycin antisera was applied to the sections followed by a biotinylated goat anti-rabbit IgG antisera. This was then followed by the addition of a biotinylated HRP/avidin mixture and enzymatic detection of HRP.

The results indicate that both the OX-26 antibody and the conjugated adriamycin localized to the rat brain capillary endothelial cells after in vivo administration. There is no evidence that free adriamycin binds to brain capillary endothelial cells or enters the brain.

An adriamycin-OX-26 conjugate coupled via a carbodiimide linkage was also synthesized (drug/antibody ratio of 10/1) and tested in vivo. The results of this experiment were essentially identical to that obtained with the periodate-linked antibody-drug conjugate. In both cases, staining for the antibody carrier was quite strong and was visualized in the capillaries in all areas of the brain. This staining was evenly distributed along the capillaries. Staining for adriamycin was less intense but again was seen in capillaries throughout the brain. Some punctate staining was observed which suggests accumulation in pericytes which lie on the brain side of the blood-brain barrier.

EXAMPLE 6

In Vivo Delivery of Methotrexate to the Brain by Murine Monoclonal Antibody OX-26.

A noncleavable carbodiimide linkage was used to couple methotrexate to the OX.26 murine monoclonal antibody. A system analogous to that described in Example 5 was used to monitor the delivery of both the methotrexate and the carrier antibody to the brain capillary endothelial cells.

Methotrexate was coupled to murine monoclonal antibody OX-26 via its active ester. Briefly, 81 mg (0.178 mM) of methotrexate (Aldrich) was stirred with 21 mg (0.182 mM) of N-hydroxysuccinimide (Aldrich) in 3 ml of dimethylformamide (DMF) at 4° C. Ethyl- 3 -dimethylaminopropyl-carbodiimide (180 mg;EDC;0.52mM) was added to this solution and the reaction mixture was stirred overnight. The crude ester was purified from the reaction by-products by flash chromatography over silica gel 60 (Merck) using a solution of 10% methanol in chloroform as an eluant. The purified active ester fractions were pooled and concentrated to dryness. The ester was dissolved in 1 ml of DMF and stored at $-20°$ C. until use. 50 mg (50%) of active ester was recovered as determined by $A_{37\text{-}2(e372=7200)}$.

A solution of OX.26 containing 2.1 mg (14 nmoles) of antibody in 0.9 ml of 0.1 M phosphate (pH 8.0) was thawed to 4° C. To this stirred antibody solution was added 1.4 $\mu$L (140 nmoles) of the active ester prepared as described above. After 16 hours at 4° $\mu$C., the mixture was chromatographed over Sephadex PD.10 column (Pharmacia) using phosphate buffered saline (PBS) to separate conjugate from free drug. The fractions containing the antibody-methotrexate conjugate were pooled. Antibody and drug concentration were determined spectrophotometrically as described by Endo et al. (*Cancer Research* (1988) 48:3330.3335). The final conjugate contained 7 methotrexates/antibody.

The ability of the OX-26 monoclonal antibody to deliver methotrexate to the rat brain capillary endothelial cells was tested in vivo by injecting 0.2 mg of conjugate (in 400 $\mu$l ) into each of two rats via the tail vein. The animals were sacrificed one hour post-injection and the brains processed for immunohistochemistry as described in Example 1. To detect methotrexate in the brain, a rabbit antisera raised against methotrexate was used as the primary antibody. A biotinylated goat anti-rabbit antisera in conjunction with a mixture of biotinylated HRP and avidin was then used to visualize methotrexate in the rat brain. The carrier antibody was detected as described previously.

The results of these experiments indicate that methotrexate in the form of a conjugate with OX-26 does accumulate along or in the capillary endothelial cells of the brain. The staining observed for methotrexate is comparable in intensity to that seen for the carrier. The staining appears to be in all areas of the brain and is evenly distributed along the capillaries.

EXAMPLE 7

Antibody Derivatives

The Fc portion of the OX.26 murine monoclonal antibody was removed to determine whether this would alter its localization to or uptake by the rat brain capillary endothelial cells. F(ab)$_2$ fragments of OX-26 were produced from intact IgG's via digestion with pepsin. A kit available from Pierce Chemical Co. contains the reagents and protocols for cleaving the antibody to obtain the fragments. The F(ab')$_2$ fragment (0.2 mg doses) in 400 $\mu$l aliquots were injected into rats via the tail vein. A time course experiment identical to that done with the intact antibody (Example 2) was then performed. F(ab')$_2$ fragment was detected immunohistochemically using a goat anti-mouse F(ab')$_2$ antisera followed by a biotinylated rabbit anti-goat IgG antisera. A biotinylated HRP/avidin mixture was added and the antibody complex was visualized using an HRP enzymatic assay. The results indicate that the F(ab)$_2$ fragment of the OX.26 antibody binds to the capillary endothelial cells of the rat brain.

EQUIVALENTS

Those skilled in the art will know, or be able to ascertain using no more than routine experimentation many equivalents to the specific embodiments expressly described herein. These are intended to be within the scope of the invention as described by the claims herein.

I claim:

1. A method for delivering a therapeutically effective amount of neuropharmaceutical agent across the blood brain barrier of a mammal comprising administering to the mammal antibody-neuropharmaceutical agent conjugate under conditions whereby said conjugate binds to transferrin receptors on brain capillary endothelial cells and transports said neuropharmaceutical agent across the blood brain barrier of the mammal in a pharmaceutically active form and in a therapeutically effective amount.

2. A method of claim 1 wherein the antibody portion of said conjugate comprises a monoclonal antibody which binds to transferrin receptor on brain capillary endothelial cells.

3. A method of claim 2 wherein said neuropharmaceutical agent is linked to the antibody via a cleavable link.

4. A method of claim 3 wherein the cleavable link is formed using cis-aconitic acid, cis-carboxylic alkatrienes or poly-maleic anhydride.

5. A method of claim 2 wherein said neuropharmaceutical agent is linked t the antibody via a noncleavable link.

6. A method of claim 5 wherein the noncleavable link is an amide bond, a bond between a sulfhydryl group and a maleimide derivative, a bond between a thiol and an amino group or a bond between an aldehyde and an amino group.

7. A method of claim 1 wherein the antibody portion of said conjugate comprises a biologically functional antibody fragment.

8. A method for delivering a therapeutically effective amount of neuropharmaceutical agent across the blood brain barrier of a mammal comprising administering to the mammal antibody-neuropharmaceutical agent conjugate under conditions whereby said conjugate binds to transferrin receptors on brain capillary endothelial cells and transports said neuropharmaceutical agent across the blood brain barrier of the mammal in a pharmaceutically active form and in a therapeutically effective amount and wherein said neuropharmaceutical agent comprises a protein.

9. A method of claim 8 wherein the antibody portion of said conjugate comprises a monoclonal antibody which binds to transferrin receptor on brain capillary endothelial cells.

10. A method of claim 9 wherein the antibody portion of said conjugate comprises a biologically functional antibody fragment.

11. A method for delivering a therapeutically effective amount of neuropharmaceutical agent across the blood brain barrier of a mammal comprising administering to the mammal antibody-neuropharmaceutical agent conjugate under conditions whereby said conjugate binds to transferrin receptors on brain capillary endothelial cells and transports said neuropharmaceutical agent across the blood brain barrier of the mammal in a pharmaceutically active form and in a therapeutically effective amount and wherein said neuropharmaceutical agent comprises a peptide.

12. A method of claim 11 wherein the antibody portion of said conjugate comprises a monoclonal antibody which binds to transferring receptor on brain capillary endothelial cells.

13. A method of claim 12 wherein the antibody portion of said conjugate comprises a biologically functional antibody fragment.

* * * * *